(12) United States Patent
Janka

(10) Patent No.: US 9,683,962 B2
(45) Date of Patent: Jun. 20, 2017

(54) APPARATUS FOR MONITORING PARTICLES IN AN AEROSOL

(75) Inventor: Kauko Janka, Tampere (FI)

(73) Assignee: Pegasor Oy, Tampere (FI)

( * ) Notice: Subject to any disclaimer, the term of this patent is extended or adjusted under 35 U.S.C. 154(b) by 281 days.

(21) Appl. No.: 13/977,116

(22) PCT Filed: Dec. 28, 2011

(86) PCT No.: PCT/FI2011/051159
§ 371 (c)(1),
(2), (4) Date: Nov. 25, 2013

(87) PCT Pub. No.: WO2012/089924
PCT Pub. Date: Jul. 5, 2012

(65) Prior Publication Data
US 2014/0069169 A1    Mar. 13, 2014

(30) Foreign Application Priority Data
Dec. 31, 2010   (FI) ..................................... 20106395

(51) Int. Cl.
*G01N 37/00*   (2006.01)
*G01N 27/62*   (2006.01)
(Continued)

(52) U.S. Cl.
CPC ........... *G01N 27/62* (2013.01); *G01N 1/2252* (2013.01); *G01N 15/0656* (2013.01)

(58) Field of Classification Search
CPC ... G01N 15/0656; G01N 1/2252; G01N 27/62
(Continued)

(56) References Cited

U.S. PATENT DOCUMENTS

| 3,526,828 A | 9/1970 | Whiby |
| 2006/0150754 A1 | 7/2006 | Burtscher et al. |

(Continued)

FOREIGN PATENT DOCUMENTS

| EP | 1655595 A1 | 5/2006 |
| FI | WO 2009/109688 | * 11/2009 |

(Continued)

OTHER PUBLICATIONS

Finnish Patent Office Search Report, Finnish patent application No. 20108395, dated Aug. 10, 2011.
(Continued)

*Primary Examiner* — John Fitzgerald
*Assistant Examiner* — Truong Phan
(74) *Attorney, Agent, or Firm* — Marshall, Gerstein & Borun LLP

(57) ABSTRACT

The present invention relates to an apparatus (1) for monitoring particles in a channel (11) or a space comprising aerosol and to an ion trap arrangement in the apparatus. The apparatus (1) comprises an ejector (24), gas supply (6, 16, 18, 19) arranged to feed an essentially particle free ionized gas flow (C) to the ejector (24), a sample-inlet arrangement (2) arranged to provide a sample aerosol flow (A) from the channel (11) into the ejector (24) by means of suction provided by the gas supply (6, 16, 18, 19) and the ejector (24) for charging at least a fraction of the particles of the sample aerosol flow (A), and an ion trap (12) extending at least partly into ejector (24) for removing ions not attached to the particles. According to the invention the ion trap (12) is a provided as a metal trap wire.

6 Claims, 3 Drawing Sheets

(51) Int. Cl.
*G01N 1/22* (2006.01)
*G01N 15/06* (2006.01)

(58) Field of Classification Search
USPC .................. 73/28.02, 28.01; 324/71.4, 464
See application file for complete search history.

(56) References Cited

U.S. PATENT DOCUMENTS

| | | |
|---|---|---|
| 2006/0156791 A1 | 7/2006 | Tikkanen et al. |
| 2006/0284077 A1* | 12/2006 | Fissan et al. ............... 250/288 |
| 2007/0056395 A1 | 3/2007 | Bae et al. |
| 2008/0137065 A1 | 6/2008 | Oberreit et al. |

FOREIGN PATENT DOCUMENTS

| | | |
|---|---|---|
| JP | 60209167 A | 10/1985 |
| JP | 2007-514923 A | 6/2007 |
| JP | 2008-542721 A | 11/2008 |
| JP | 50-56293 B2 | 10/2012 |
| WO | WO-2009109688 A1 | 9/2009 |

OTHER PUBLICATIONS

International Search Report for corresponding international application No. PCT/FI2011/051159, dated Apr. 3, 2012.
Romay et al., A sonic jet corona ionizer for electrostatic discharge and aerosol neutralization, Aerosol Sci. Tech., 20(1):31-41 (1994).
Office Action (English translation), Japanese Patent Application No. 2013-546748, dated Jun. 11, 2015.
Notification of the Reasons for Rejection (English translation), Korean patent application No. 10-2013-7020265, mailed Jul. 30, 2015.

* cited by examiner

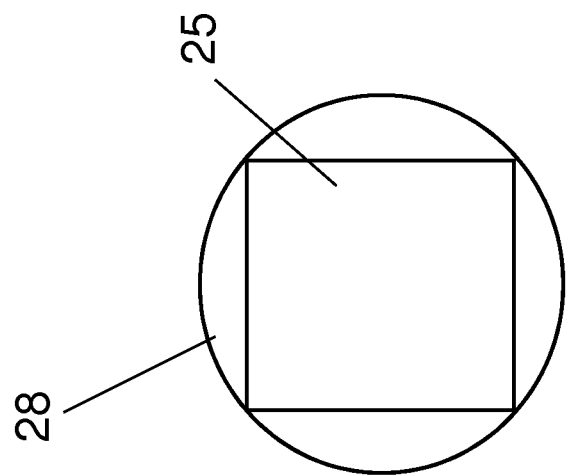

APPARATUS FOR MONITORING PARTICLES IN AN AEROSOL

FIELD OF THE INVENTION

The present invention relates to an apparatus for monitoring particles and especially to an apparatus as defined in the preamble of independent claim 1.

BACKGROUND OF THE INVENTION

Fine particles having diameter are formed in many industrial processes and combustion processes. For various reasons these fine particles are measured. The fine particle measurements may be conducted because of their potential health effects and also for monitoring operation of industrial processes and combustion processes, such as operation of combustion engines, especially diesel engines. Another reason for monitoring fine particles is the increasing use and production of nanosized particles in industrial processes. The above reasons there is need for reliable fine particle measurement equipments and methods.

One prior art method and apparatus for measuring fine particles is described in document WO2009109688 A1. In this prior art method clean, essentially particle free, gas is supplied into the apparatus and directed as a motive fluid flow via an inlet chamber to an ejector provided inside the apparatus. The clean gas is further ionized before and during supplying it into the inlet chamber. The ionized clean gas may be preferably fed to the ejector at a sonic or close to sonic speed. The ionizing of the clean gas may be carried out for example using a corona charger. The inlet chamber is further provided with a sample inlet arranged in fluid communication with a channel or a space comprising aerosol having fine particles. The motive fluid flow (i.e. the clean gas flow) causes suction to the sample inlet such that a sample aerosol flow is formed from the duct or the space to the inlet chamber. The sample aerosol flow is thus provided as a side flow to the ejector. The ionized clean gas charges at least a fraction of the particles. The charged particles may be further conducted back to the duct or space containing the aerosol. The fine particles of the aerosol sample are thus monitored by monitoring the electrical charge carried by the electrically charged particles. Free ions are further removed using an ion trap arranged downstream of the ejector. A typical ejector (or ejector pump) includes a diverging cone (or diverging outlet diffuser) after the narrow throat to convert the kinetic energy of the gas to pressure. This increases the the size and residence time of the gas inside the ejector. The residence-time increase slowers the time response of the measurement apparatus based on the prior-art method (WO2009109688 A1).

One important demand for the fine particle monitoring apparatuses is reliable operation such that they may be operated long time periods without need for maintenance. In many applications, such as monitoring fine particles of combustion engines, it is also preferable that the monitoring apparatus may be operated continuously for conducting fine particle measurements in real-time. Furthermore, in many cases the fine particle monitoring apparatuses have to be installed in existing systems in which there is only limited amount of space for the particle measurement apparatus. Usually industrial systems, combustion systems or other aerosol comprising systems are designed as compact as possible. Therefore, the fine particle measurement apparatus also has to be small sized. The advantage of the small size is not, however, restricted only to the use of limited space.

A more important advantage of the small size is the minimization of particle losses into the measurement apparatus. Further, small size enables faster time response of the measurement due to the faster gas flow through the small sensing volume.

In many cases it's important that manufacturing costs of the apparatus is low. For this reason the structure of the apparatus should not be too complex to fabricate.

BRIEF DESCRIPTION OF THE INVENTION

The object of the present invention is to provide an apparatus and arrangement so as to overcome the prior art disadvantages. The objects of the present invention are achieved with an apparatus according to the characterizing portion of claim 1, which apparatus comprises an ion trap 12 provided as a trap wire.

The preferred embodiments of the invention are disclosed in the dependent claims.

The present invention is based on the idea of providing an apparatus for monitoring particles of an aerosol by charging at least a fraction of the particles with an essentially particle free ionized gas fed into an ejector and removing ions not attached to the particles substantially downstream of the ejector with an ion trap formed as wire or rod. The ion trap wire may be straight or it may be bended to a curved configuration. The trap wire extends at least partly into the ejector. In one embodiment the trap wire is arranged to extend at least partly into the throat of the ejector. When the trap wire extends into the throat (preferably the diverging part of it), the ion trap utilizes the ejector structures and inner volume. As a result the total size of the measuring apparatus and the sample-gas residence time in the sensor can be reduced. The reduced residence time enables faster time response of the measurement apparatus.

Wire or rod-based ion traps are known as such from the prior art. US patent application 2006/0284077 A1, TSI Incorporated, 21 Dec. 2006, describes an instrument for non-invasively measuring nanoparticle exposure includes a corona discharge element generating ions to effect unipolar diffusion charging of an aerosol, followed by an ion trap for removing excess ions and a portion of the charged particles with electrical mobilities above a threshold. Preferably the higher electrical mobility elements are extracted using an electrostatic precipitator with a tubular electrically conductive structure that surrounds a conductive element electrically isolated from the structure. The publication fails, however, to describe the advantages which are achievable by using an ejector and thus the instrument may suffer from particle losses.

The advantage of an ejector in a particle measurement apparatus which is based on the measurement of electrical charge carried by particles is that it allows a fast mixing of ions and particles. An ejector typically consists of three parts: inlet nozzle, throat and diverging outlet diffuser. The inventor has found that mixing of the motive fluid flow and the side flow in an ejector is so efficient that in practice the particles are charged by the ions carried by the motive fluid flow latest in the throat of the ejector. Thus the ion trap used to remove the excess ions from the flow may be assembled at least partly into the ejector and thus considerably shorten the flow path and minimize the size of the particle monitoring apparatus. This also minimizes particle losses into the particle measurement apparatus and enables faster time response of the apparatus. Preferably, especially in the case of cylindrically symmetric structure, the high-voltage electrode of the ion trap is rod-shaped, most preferably a wire, which does not essentially affect the flow pattern inside the particle measurement apparatus. The ejector surfaces, especially the inner surface of the diverging diffuser and in some cases also the inner surface of the throat, work as the ion collecting electrodes.

In a preferred embodiment of the present invention the ion trap is formed as a single wire or a rod providing both the ion trap wire and the ion trap conductor. The ion trap is arranged to extend inside the measurement housing from the inlet chamber to the ion trapping chamber and to the ejector in which it forms the ion trap.

The present invention has the advantage that the ion trap wire provides a simple mechanical structure for the ion trap. The simple mechanical structure enhances the reliable operation such that the apparatus for monitoring particles or the particle sensor may be operated long time periods without need for maintenance. The ion trap arrangement in which the trap conductor extends inside the measurement housing from the inlet chamber to the ion trapping chamber and ejector provides also a compact structure and decreases the external dimensions or diameter of the apparatus. The trap wire may also be formed into a configuration which enables decreasing the dimensions of the ion trapping housing and thus the external dimensions or the length of the apparatus. The trap wire may also be formed into a configuration which enables use of moderate ion trapping voltages.

BRIEF DESCRIPTION OF THE FIGURES

In the following the invention will be described in greater detail, in connection with preferred embodiments, with reference to the attached drawings, in which

FIG. 3 is a schematic view of one embodiment of an ion trap conductor.

DETAILED DESCRIPTION OF THE INVENTION

Figure 1:
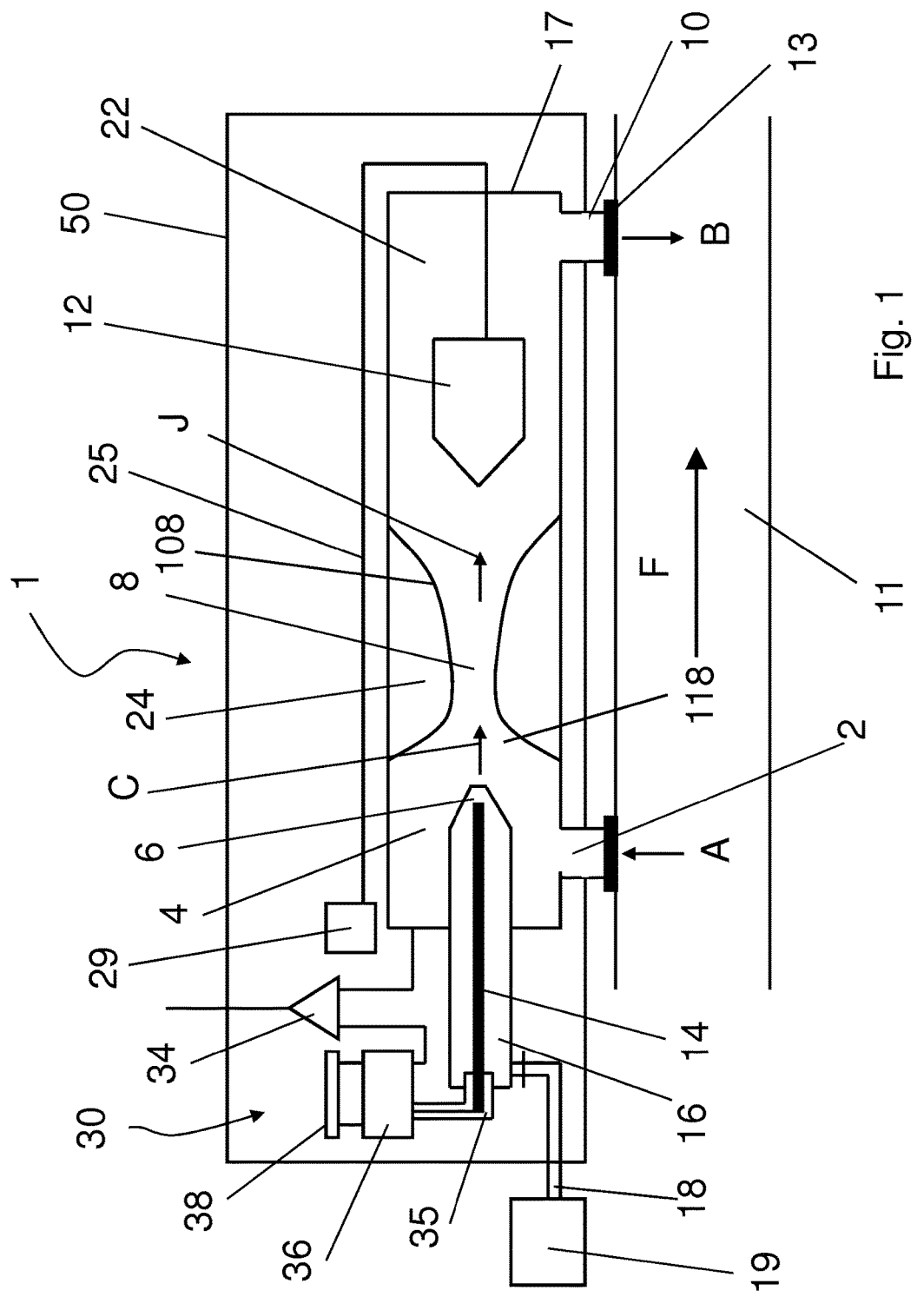
FIG. 1 is a schematic view of a prior part apparatus for monitoring particles.

The FIG. 1 shows one embodiment of a prior art apparatus for monitoring particles. The apparatus comprises an outer body 50 inside which is provided a measurement housing 17 and at least part of the electrical components and conductors 30 of the apparatus. As seen in FIG. 1 the electrical components and connectors 30 are arranged substantially outside of the measurement housing 17, thus between the outer body 50 and the measurement housing 17.

The measurement housing 17 provides space in which the particles monitoring of the aerosol is conducted. A sample aerosol flow A is guided from a channel, duct or a space comprising aerosol inside the measurement housing 17 for monitoring or measuring particles in the aerosol. The apparatus 1 is connected to an aerosol duct 11 in side which is an aerosol flow F. Thus the apparatus 1 is arranged to monitor fine particles or particles in the aerosol flow F. The aerosol duct may be exhaust duct of a combustion engine or the like. Alternatively aerosol duct may be any space comprising aerosol or any duct or channel having an aerosol flow F. The space does have to comprise an aerosol flow, but the apparatus may also be arranged to monitor particles of a substantially stationary aerosol for example particles of indoor air. In figures the particle monitoring apparatus is connected outside of the aerosol duct 11 and to the side wall of the aerosol duct 11. This configuration needs openings to be made to the side walls of the duct 11, but the apparatus does not significantly affect the flow conditions inside the duct 11. In another embodiment the particle monitoring apparatus may be located inside the aerosol duct 11. In this embodiment the apparatus may connected to the inner side walls of the duct 11 and no openings have to be made to the side walls of the duct. The apparatus may be located inside an aerosol duct, or an exhaust duct, for example when it is used to monitor particles of the exhaust gas of a combustion engine.

The apparatus 1 comprises a sample inlet 2 for guiding a sample aerosol flow A into the apparatus 1. The sample inlet 2 is in fluid communication with the aerosol duct 11 and inside of the measurement housing 17 of the apparatus 1. The apparatus 1 preferably also comprises a sample outlet 10 through which the analyzed sample aerosol flow B is exhausted from the measurement housing 17 and the apparatus 1. In the embodiment of FIG. 1 the analyzed sample aerosol B is returned to the aerosol duct 11. The sample outlet 10 may also be arranged to conduct the analyzed sample aerosol B directly to the ambient atmosphere or some other location, for example a container. Accordingly the apparatus 1 does not necessarily collect or store the sample aerosol A received from the aerosol duct 11. In an alternative embodiment the apparatus may also comprise a sample-inlet arrangement 2 comprising one or more sample inlets. Furthermore the apparatus may also comprise a sample outlet arrangement 10 comprising one or more sample outlets.

The apparatus 1 comprises an inlet chamber 4 and the sample inlet 2 is arranged to provide a fluid communication between the aerosol duct 11 and the inlet chamber 4. The apparatus further comprises a gas supply for supplying clean particle free gas C into the inlet chamber 4. The gas supply comprises gas supply connection 18 via which the clean gas may be brought from a gas source 19. The gas may be cleaned in a filter or the like for essentially removing particles from the gas such that the particle concentration in the pressurized gas is remarkably lower than the particle concentration in the sample aerosol flow A. The clean gas may be air or some other suitable gas. The clean gas may be also further conditioned before feeding it into the inlet chamber 4. The conditioning may comprise cooling or heating the gas and adjusting the gas flow speed and volume with a flow controller. The clean gas is then fed to the measurement apparatus 1 through the gas supply connection 18.

The apparatus 1 further comprises a clean gas supply channel 16 through which the clean gas is fed to inlet chamber 4 of the apparatus 1. The clean gas supply channel 16 is in fluid communication with the gas supply channel 18 and comprises a nozzle head 6 opening into the inlet chamber 4. The apparatus is further provided with an ionization device 14 for ionizing at least a portion of the clean gas before or during feeding the clean gas from the nozzle head 6 into the inlet chamber 4. In the embodiment of FIG. 1 the ionization device 14 is arranged to the clean gas supply channel 16. In the embodiment of FIG. 1 the ionization device is a corona needle 14 extending in the clean gas supply channel 16. the ionization device 14 may also be another kind of electrode suitable for ionization the clean gas. The nozzle head 6 and the corona needle 14 are advantageously arranged such that corona needle 14 extends essentially to the vicinity of the nozzle head 6. This helps the corona needle 14 to stay clean and improves the ion production. The clean gas flow passing the corona needle 14 keeps the corona needle clean. The corona needle 14 is isolated from the clean gas flow channel walls and the body 17 of the apparatus 1 by one or more electrical insulators 35. The walls of the gas supply channel 16 are preferably at the same potential as the corona needle 14. According to the above mentioned the gas supply channel 16 is arranged to provide an essentially particle free ionized gas flow C to the inlet chamber 4.

The apparatus is further provided with an ejector 24. The ejector 24 comprises a converging-diverging nozzle 24 forming thus a converging-diverging flow channel, the throat 8 of the ejector 24. The ejector 24 is a pump-like device utilizing the momentum of the main flow to create suction for a side fluid flow. The main fluid flow and the side fluid flow are at least partly mixed in the ejector 24. After passing through the throat 8 of the ejector 24, the mixed fluid expands and the velocity is reduced which results in converting kinetic energy back into pressure energy. In an alternative embodiment the apparatus may also comprise one or more clean gas supply channels 16, corona needles 14 and ejectors 24.

In the embodiment of FIG. 1 the essentially particle free ionized gas flow C discharged from the nozzle 6 is fed to the throat 8 of the ejector 24 as a main flow. Therefore the clean gas supply channel 16 and the nozzle head 6 are arranged to feed the essentially particle free gas flow C at a high velocity into the throat 8. The velocity of the essentially particle free gas flow C is preferably sonic or close to sonic. In the ejector 24 the essentially particle free gas flow C forms a suction to the sample inlet 2 such that the sample aerosol flow A may be sucked into the inlet chamber 4. The sample aerosol flow A forms a side flow of the ejector 24. The flow rate of the sample aerosol flow A is depended essentially only on the geometry of ejector 24 and the flow rate of the essentially particle free ionized gas flow C. In a preferred embodiment the ratio of the main flow C to the side flow A is small, preferably less than 1:1 and more preferably less than 1:3. According to the above mentioned there is no need for actively feed the sample aerosol flow A into the apparatus 1, but it may be sucked by the by means of the clean gas supply and the ejector 24.

The essentially particle free ionized gas flow C and the sample aerosol flow are mixed in the inlet chamber 4 and in the ejector 24 such that the particles of the sample aerosol flow A are electrically charged during the mixing by the ionized clean gas flow C. The essentially particle free ionized gas flow C and the sample aerosol flow A form together an ejector flow J discharging from the ejector 25 and specifically from throat 8 of the ejector 24. The apparatus 1 further comprises ion trapping chamber 22 in side the measurement housing 17. The ion trapping chamber 22 comprises an ion trap 12 for removing ions that are not attached to the particles of the sample aerosol flow A. The ion trap 12 may be provided with a collection voltage for removing the mentioned free ions. The voltage used for trapping free ions depends on design parameters of the apparatus 1, but typically the ion trap 12 voltage is 10 v-30 kV. The ion trap 12 voltage may also be adjusted to removed nuclei mode particles or even the smallest particles in the accumulation mode. In an alternative embodiment the ion trap 12 is arranged to remove ions not attached to the particles from the ejector flow J by an electric field, magnetic field, diffusion or a combination thereof.

The sample aerosol and the essentially clean gas mixed together, the ejector flow J, are discharged from the apparatus 1 through the outlet 10 together with the charged particles of the sample aerosol. The outlet 10 is provided in fluid communication with the ion trapping chamber 22 for exhausting the discharge flow B out of the apparatus 1. The outlet 10 may be arranged to supply the discharge flow B back to the aerosol duct 11 or to ambient atmosphere or some other location.

Particles of the aerosol F in the aerosol duct 11 are monitored by measuring the electrical charge carried by the electrically charged particles of the sample aerosol flow A. In a preferred embodiment the particles of the aerosol F are monitored by measuring the electrical charge escaping with the electrically charged particles from the apparatus 1 with the ejector flow J through the outlet 10. The measurement of the charge carried by the electrically charged particles may be measured by many alternative ways. In one embodiment the charge carried by the electrically charged particles is measured by measuring the net current escaping from the sample outlet 10. To be able to measure the small currents, typically at pA level, the whole apparatus 1 is isolated from the surrounding systems. In FIG. 1 the apparatus 1 is provided with installation insulators 13 for insulating the apparatus 1 from the duct 11. An electrometer 34 may be assembled between the isolated apparatus 1 (i.e. a pint in the wall of body 50) and a ground point of the surrounding systems. With this kind of setup, the electrometer 34 may measure the charge escaping from the isolated apparatus 1 together with the ionized particles. In other words this kind of setup measures the escaping current.

FIG. 1 shows one embodiment for monitoring the particles by measuring the current escaping from the apparatus 1. The escaping current is measured with electrical arrangement 30. The electrical arrangement 30 comprises a high voltage source 36 connected to the ionization device 14 for providing a high voltage to the ionization device 14. The high voltage source 36 is electrically isolated from the other system via an isolating transformer 38 and electrical insulators 35. The ionization device 14 is in the same electrical potential as the walls of the gas channel 16. The electrical arrangement 30 comprises further an electrometer 34 assembled between the ionization device 7 and to a point having a galvanic contact with the wall of the measurement housing 17. First contact of the high voltage source 36 is connected to the ionization device 14 and the second contact is connected as a first input of the electrometer 34. The second input of the electrometer 34 is connected to the wall of the measurement housing 17 and to the ion trap 12. With this kind of electrical arrangement 30, the electrometer 34 measures the charge escaping from the ion trapping chamber 22 and from the apparatus 1 with the ionized particles, e.g. measures the escaping current.

The ion trap 12 prevents the free ions escaping from the apparatus 1. The ion trap 12 is connected to a collection voltage source 29 via an ion trap conductor 25. In the prior art the ion trap 12 is provide as net-like electrodes or plate like electrodes. FIG. 1 shows one prior art embodiment in which the ion trap 12 plate arrangement arranged downstream of the ejector 24 for removing free ions from the ejector flow J. The ion trap 12 is connected to a collection voltage source 29 via the ion trap conductor 25 arranged to extend from substantially outside of the measurement housing 17 and specifically between the outer body 50 and the measurement housing 17 of the apparatus 1. In an alternative embodiment the ion trap may be arranged to remove ions not attached to the particles from the ejector flow J by an electric field, magnetic field, diffusion or a combination thereof.

FIG. 2 shows one embodiment of the present invention. In FIG. 2 the trap wire 12 is bended to extend at least partly into the ejector 24, which consists of the inlet nozzle 118, throat 8 and diverging diffuser 108. Specifically the trap wire 12 is arranged to extend at least partly into the throat 8 of the ejector 24 or at least partly into a diffuser part 108 of the ejector 24. This configuration of FIG. 2 enables the diffuser 108 or the throat 8 of the ejector 24 to be used for removing free ions not attached to the particles. Therefore, the trap wire 12 utilizes the length of the ejector 24 such that the length of the apparatus and specifically the length of the ion trapping chamber 22 may be shortened. In tests it has been surprisingly noticed that the charging of the particles is not affected when the trap wire 12 extends at least partly into the ejector 24 as that the ionization of the particles is carried out well before the exit of the ejector 24.

Figure 2:
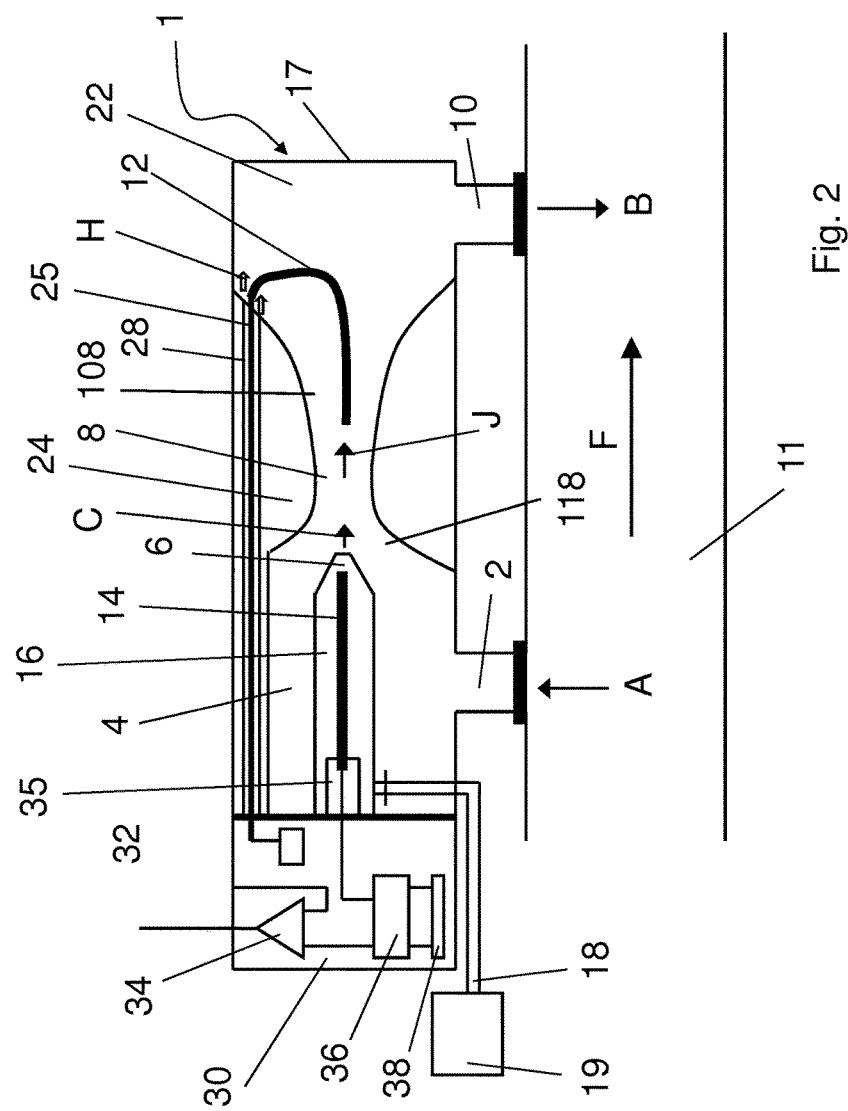
FIG. 2 is a schematic view of one embodiment of an apparatus for monitoring particles according to the present invention.

As seen in FIG. 2, the apparatus 1 forming a particle sensor comprises a measurement housing 17 inside which the ejector 24 is provided. The inlet chamber 4 is arranged upstream of the ejector 24 and inside the measurement housing 17. The inlet chamber 17 is provided with the gas supply 6, 16, 18, 19 feeding an essentially particle free ionized gas flow C to the ejector 24 for providing a sample aerosol flow A through a sample-inlet arrangement 2 from a channel 11 or a space. The ion trapping chamber 22 is arranged downstream of the ejector 24 and inside the measurement housing 17. The ion trapping chamber 22 is provided with an ion trap arrangement 12, 25, 26 comprising an ion trap 12 connected to a collection voltage source 29 with a trap conductor 25 for providing the ion trap 12 with a collection voltage for removing ions not attached to the particles from an ejector flow J. The collection voltage source 29 is located outside the measurement housing 17. As shown in FIG. 2, the trap conductor 25 is arranged to extend inside the measurement housing 17 and specifically in side the measurement housing 17 from the inlet chamber 4 to the ion trapping chamber 22 for providing the collection voltage to the ion trap 12. In one embodiment the trap conductor 25 is arranged to extend inside the measurement housing 17 and specifically in side the measurement housing 17 through the inlet chamber 4 and the ejector structure 24 to the ion trapping chamber 22 for providing the collection voltage to the ion trap 12

The trap conductor 25 is electrically insulated from the measurement housing 17. The trap conductor 25 may be provided with an outer insulation layer for insulating purposes. The measurement housing 17 may be provided with a trap conductor channel 28 through which the trap conductor 25 is passed inside the measurement housing 17 for separating the trap conductor (25) from the sample aerosol flow A, essentially particle free ionized gas flow C and the ejector flow J. The trap conductor channel 28 may provide an electrical insulation for the trap conductor 25 inside the measurement housing 17. As shown in FIG. 2, the trap conductor channel 28 may extend from the inlet chamber 4 to the ion trapping chamber 22 or through the inlet chamber 4 and the ejector structure 24 to the ion trapping chamber 22 such that the trap conductor 25 may be passed inside the measurement housing 17 to the ion trapping chamber 22 such that the trap conductor 25 is not subjected to the sample aerosol A and to the essentially particle free ionized gas flow C. The ejector 24 may be formed from a ceramic material. The ceramic material of the ejector 24 may be arranged to extend through the whole inlet chamber 4 such that the trap conductor channel 28 may be provided to the ceramic material. The trap conductor channel 28 may thus extend through the ceramic material from the electronic arrangement through the inlet chamber and the ejector structure into the ion trapping chamber 22. The trap conductor channel 28 may be formed by boring it through the ceramic material. When ceramic material is used to form the ejector 24, the ceramic material may be coated with an electrically conductive layer, such as a metal layer. The electrically conductive coating is further in connection with the walls of the measurement housing 17 such that the ceramic material is in the same potential with the measurement housing 17. In an alternative embodiment the ceramic material may be replaced with some other material. In a yet alternative embodiment the trap conductor channel 28 may be provided with a separate channel element arranged inside the measurement housing 17. The trap conductor channel 28 prevents the trap conductor 25 from soiling due to the sample aerosol flow A.

The trap conductor channel 28 may become contaminated as contaminants, such as fine particles of the sample aerosol, may enter the trap conductor channel 28 via the opening from which the ion trap 12 or an ion trap holder 26 extends into the ion trapping chamber 22. The ion trap holder 26 may any mechanical and electrically conductive part arranged to support the ion trap 12 and to conduct the collection voltage from the ion trap conductor 25 to the ion trap 12. The ion trap holder 26 may be a separate part or it may be an integral part of the ion trap conductor 25 or the ion trap 12 or both. To prevent soiling of the trap conductor channel 28 it may be provided with a sheath gas flow H flowing along the trap conductor channel 28 to the ion trap chamber 22 between the inner walls of the trap conductor channel 28 and the trap conductor 25. The sheath gas flow H may comprise any suitable gas from any suitable gas source. In a preferred embodiment the sheath gas flow H is provided from the gas source 19 supplying also the essentially particle free gas flow to the inlet chamber 4. The trap conductor channel 28 and the ion trap conductor 25 have preferably different cross-sectional shapes for provided a gap between the trap conductor channel 28 and the ion trap conductor 25 in which gap the sheath flow H flows. FIG. 3 shows one embodiment in which the trap conductor channel 28 has a substantially round cross-section and the ion trap conductor 25 a substantially rectangular cross-section.

The ion trap 12 may be a separate element electrically connected to the trap conductor 25 with or without a trap holder 26. The separate ion trap 12 may be ion trap plate, net or some other substantially three dimensional ion trap arrangement.

In a preferred embodiment of the present invention the ion trap 12 and the trap conductor 25 are provided as a single metal wire or a rod without a trap holder 26. The ion trap or the trap wire 12 may be implemented as described earlier. Thus the trap wire 12 extends in the trap conductor channel 28 as an ion trap conductor from which it is enters into the ion trapping chamber 22 as an ion trap 12. This provides a simple and compact solution for the ion trap arrangement. In this kind of ion trap arrangement the ion trap 12 may be longitudinal wire or a rod arranged to extend at least partly into the ejector 24 or at least partly into the throat 8 of the ejector 24 inside the ion trapping chamber 22.

It is apparent to a person skilled in the art that as technology advanced, the basic idea of the invention can be implemented in various ways. The invention and its embodiments are therefore not restricted to the above examples, but they may vary within the scope of the claims.

The invention claimed is:

1. An apparatus for monitoring particles in a channel or a space comprising an aerosol, the apparatus comprising:

an ejector;

a gas supply that is arranged to feed an essentially particle-free ionized gas flow to the ejector;

a sample-inlet arrangement that is arranged to provide a sample aerosol flow from the channel or the space into the ejector by means of suction provided by the gas supply and the ejector, causing at least a fraction of the particles in the sample aerosol flow to become charged;

an ion trap that removes ions that are not attached to the particles from an ejector flow that discharges from the ejector; and an electrometer for measuring the charge escaping from the ion trap;

wherein the ion trap comprises a trap wire that extends at least partly into the ejector and comprises a trap conductor that connects the trap wire to a collection voltage source for removing the ions not attached to the particles, and the trap conductor is arranged to extend inside a measurement housing from an inlet chamber to an ion trapping chamber.

2. The apparatus according to claim 1, wherein the trap wire and the trap conductor are provided as a single metal wire or a rod.

3. The apparatus according to claim 1, wherein the trap conductor is arranged to extend in a trap conductor channel.

4. The apparatus according to claim 3, wherein the trap conductor channel is provided with a sheath gas flow that flows to the ion trapping chamber between the inner walls of the trap conductor channel and the trap conductor.

5. The apparatus according to claim 1, wherein the trap wire comprises a trap conductor that connects the trap wire to a collection voltage source for removing the ions not attached to the particles, and the trap conductor is arranged to extend inside the measurement housing through the inlet chamber and the ejector structure to the ion trapping chamber.

6. The apparatus according to claim 5, wherein the trap conductor is arranged to extend in a trap conductor channel.

* * * * *